United States Patent
Timmins et al.

(10) Patent No.: US 8,569,060 B2
(45) Date of Patent: Oct. 29, 2013

(54) METHOD OF PRODUCING A POPULATION OF CELLS

(75) Inventors: Nicholas Eion Timmins, St. Lucia (AU); Lars Keld Nielsen, St. Lucia (AU); Emma Louise Palfreyman, Fig Tree Pocket (AU)

(73) Assignee: The University of Queensland, Queensland (AU)

( * ) Notice: Subject to any disclaimer, the term of this patent is extended or adjusted under 35 U.S.C. 154(b) by 0 days.

(21) Appl. No.: 12/812,143

(22) PCT Filed: Jan. 8, 2009

(86) PCT No.: PCT/AU2009/000014
§ 371 (c)(1),
(2), (4) Date: Jul. 8, 2010

(87) PCT Pub. No.: WO2009/086596
PCT Pub. Date: Jul. 16, 2009

(65) Prior Publication Data
US 2010/0285586 A1    Nov. 11, 2010

Related U.S. Application Data

(60) Provisional application No. 61/010,492, filed on Jan. 8, 2008.

(51) Int. Cl.
*C12N 5/02*     (2006.01)
*C12N 5/00*     (2006.01)
*C12N 5/071*    (2010.01)

(52) U.S. Cl.
USPC ........... 435/377; 435/325; 435/372; 435/373; 435/375; 435/385

(58) Field of Classification Search
None
See application file for complete search history.

(56) References Cited

U.S. PATENT DOCUMENTS

| 6,077,708 | A | 6/2000 | Collins et al. | |
| 6,326,198 | B1 * | 12/2001 | Emerson et al. | 435/373 |
| 2005/0163760 | A1 | 7/2005 | Cartier-Lacave et al. | |
| 2010/0151569 | A1 * | 6/2010 | Nielsen et al. | 435/372 |

FOREIGN PATENT DOCUMENTS

| WO | 00/45827 A1 | 8/2000 |
| WO | 03/087333 A2 | 10/2003 |
| WO | 2004/071283 A2 | 8/2004 |
| WO | 2005/007799 A2 | 1/2005 |

OTHER PUBLICATIONS

McAdams et al., Hematopoietic cell culture therapies (Part I): cell culture considerations, TIBTECH Sep. 1996 (vol. 14).*
Carswell et al., Culture of Human T Cells in Stirred Bioreactors for Cellular Immunotherapy Applications: Shear, Proliferation, and the IL-2 Receptor, Biotechnol Bioeng 68: 328-338, 2000.*
International Preliminary Report of Patentability and Written Opinion of the International Searching Authority for corresponding U.S. Application, Jan. 8, 2010.
Dang, S. M., et al., "Stem Cells", vol. 22, No. 3, pp. 275-282 (2004).
De Leon, A. et al., "Cytotechnol.", vol. 28, No. 1-3, pp. 127-138 (1998).
Zipori, D., "FASEB J.", vol. 6, No. 9, pp. 2691-2697 (1992).
Smith, B.R., "Yale J. Biol. Med.", vol. 63, No. 5, pp. 371-380 (1990).

* cited by examiner

*Primary Examiner* — Jim Ketter
*Assistant Examiner* — Reza Ghafoorian
(74) *Attorney, Agent, or Firm* — Edwards Wildman Palmer LLP; Peter F. Corless

(57) ABSTRACT

An in vitro or ex vivo method of producing a population of lineage committed haematopoietic progenitor or mature haematopoietic cells other than cells of the neutrophil lineage, including the steps of providing a population of haematopoietic progenitor cells; and culturing the haematopoietic progenitor cells in an animal cell culture medium including one or more cytokines that differentiate the haematopoietic progenitor cells into lineage committed haematopoietic progenitor and/or mature haematopoietic cells, under static conditions until the cells are at a cell density at which oxygen transfer via the surface of the culture medium is insufficient for growth of the progenitor cells and progeny thereof under static conditions, and then agitating the culture medium to produce a population of lineage committed haematopoietic progenitor or mature haematopoietic cells other than cells of the neutrophil lineage.

10 Claims, No Drawings

METHOD OF PRODUCING A POPULATION OF CELLS

This application is the U.S. National Phase Application, pursuant to 35 U.S.C. §371, of PCT International Application Serial No. PCT/AU2009/000014, filed Jan. 8, 2009, designating the United States and published on Jul. 16, 2009 as publication WO 2009/086596, which claims the benefit of U.S. Provisional application No. 61/010,492, filed Jan. 8, 2008, both of which are incorporated herein by reference in their entirety.

FIELD OF THE INVENTION

The present invention relates to methods of producing populations of committed or mature/terminally differentiated haematopoietic cells.

BACKGROUND TO THE INVENTION

The need for blood transfusions in cases of trauma is readily appreciated by most people. In a broader context, disease, deficiencies of the haematopoietic system, and insult through chemical, radiological, physical, or other means, can all have serious consequences through loss of blood, changes to the composition of blood, altered functionality of blood, and/or reduced maintenance of the circulating blood pool (homeostatic replacement and refreshment of blood and its components).

Blood is a complex biological fluid consisting of multiple cellular (e.g., erythrocytes, macrophages, lymphocytes, monocytes, platelets), and non-cellular components (e.g., plasma, immunoglobulins). In the case of cellular components, the only means through which these are currently available as a transfusable product, is through donation. Worldwide, the demand for transfusable blood products is increasing. Unfortunately this increasing demand cannot be met by the current donor system. Blood shortages are not uncommon, and loss is still a major cause of death.

Increasing stringency in donor screening, and the prevalence of blood transmissible disease such as HIV/AIDS is limiting the availability of new donors, while ageing of existing donors reduces their ability to give blood. There is also a substantial imbalance in donor availability between developed and developing/transitional regions. More than 81 million units of blood are collected each year, but only 45% of these are donated in developing or transitional countries, where greater than 80% of the world's population live.

A possible alternative to the existing blood donor system is to cultivate blood cells in vitro. By leveraging the capacity of haematopoietic stem cells to expand in number and differentiate along particular lineages in response to specific cues, it may be possible to manufacture substantial numbers of blood cells and derivatives (e.g. platelets).

In order to better understand the task of manufacturing blood cells, it is useful to understand the underlying biology of the haematopoietic system.

Human Haematopoiesis

All blood cells are derived from a common progenitor cell type known as the haematopoietic stem cell (HSC). HSC were the first human stem cell to be identified, and have been used in human therapy since the early 1950's in the form of bone marrow transplants. HSC have the ability to either self-renew, or enter a process of differentiation by which a single HSC can give rise to progeny belonging to any of the haematopoietic lineages. These lineages are broadly categorised as myeloid and lymphoid.

Cells of the myeloid lineage arise from a common myeloid progenitor and can be further categorised into erythrocytes, megakaryocytes, granulocytes, and monocytes.

Erythroid cells ultimately mature into red blood cells (erythrocytes), playing an essential role in transporting oxygen throughout the body. Megakaryocytes play a vital role in the production of cell fragments known as platelets or thrombocytes, which are essential in blood clotting. Granulocytes and monocytes are immune cells involved in both adaptive and innate immunity, with granulocytes further subdivided into neutrophils, basophils, and eosinophils. Monocytes give rise to macrophages and myeloid dendritic cells.

The lymphoid lineage consist of immune cells such B-cells, T-cells, natural killer cells, and lymphoid dendritic cells, which all play a role in adaptive immunity.

In adults, the primary site of haematopoiesis is the bone marrow. Here the HSC are believed to reside within a regulatory microenvironment or niche, which acts to maintain the HSC pool through self renewal. Progenitor cells may exit the niche and undergo a regulated process of differentiation toward mature blood cells of the lineages described previously. The HSC niche and process of differentiation are regulated by a number interacting factors. Physiochemical parameters such as dissolved oxygen and pH, the concentration of biological effectors molecules, interactions with surrounding cells, and contact with extra cellular matrix (ECM) and ECM bound factors, are all believed to a play role in the regulation HSC self-renewal and differentiation.

By identifying the specific cues required to drive differentiation towards a particular lineage, and manipulating these ex vivo in cell culture systems, it is is possible to selectively expand and differentiate HSCs into large numbers of lineage specific cells. The final cell product may be fully mature, or alternatively, a population of lineage committed, but not fully differentiated cells, can be produced.

Conditions for ex vivo production of mature blood cells from HSCs have been described, with varying degrees of success. In addition to haematopoietics, three exemplary cell types are erythrocytes, dendritic cells and megakaryocytes. A number of potential clinical uses for such ex vivo expanded haematopoietic cell populations have been proposed.

Clinically, erythrocytes, could be used to replace lost blood in cases of bleeding/trauma. Megakaryoctyes can be used to generate platelets for transfusion support in chemotherapy patients. Dendritic cells have been proposed as a means by which to train the body's immune system to recognise and attack cancer cells. Numerous other applications of ex vivo expanded blood cells are also possible, replacing or augmenting current applications for donor derived products, or representing new therapeutic avenues.

While biological cues for ex vivo expansion of haematopoietic cells have been identified, a key challenge to clinical application lies in identifying appropriate means for the large scale production of these cells. Traditional static culture systems (e.g., tissue culture flasks) cannot be readily scaled to produce clinically relevant cell numbers (e.g. at $2 \times 10^{12}$ cells, one unit of erythrocytes would require some 5000 $m^2$ of culture surface to produce in static flask cultures).

In order to reduce the required surface area per unit volume of culture, agitation can be used to induce mixing and hence enhance mass transfer of oxygen into the culture environment. In this way, large volume cultures can be conducted in compact geometries. Stirred bioreactor systems (or fermenters) can and have been used for the cultivation of haematopoietic cells. However, in these systems the extent of expansion achieved is poor and insufficient cell numbers are obtained. Alternative systems by which to deliver oxygen and nutrients within compact geometries, such as hollow fibre culture devices, suffer from additional engineering complications. Again taking the example of one unit of erythrocytes, some 1.5 km of fibre, providing a lumen volume of 50 L, would be required. This is far beyond the scale to which this approach has so far been successfully demonstrated.

In order to realise the potential of ex vivo expanded haematopoietic cells in a clinical setting, improved processes for their manufacture in substantial numbers are required.

SUMMARY OF THE INVENTION

While the demands of clinical scale expansion require vigorous culture conditions, we have found that during the early stages of expansion in cell culture haematopoietic stem cells and other progenitors are very sensitive to agitation. Progenitor cells, e.g. $CD34^+$ cells, are typically seeded at a low initial density, e.g. from about 1,000 to 10,000 cells per ml. At this density, the cells appear to be particularly sensitive to stress caused by agitation of the culture, which results in poor cell expansion and cell death. We believe that this is a result of oxidative stress and that the sensitivity appears to be related to cell density and the ratio of cells to reactive oxygen species. However, we have found that after a period of time and once the cells have reached a certain density, they can be cultured under the more vigorous conditions that exist in large scale cultures to provide high yields of lineage committed and/or mature cells. For example, it has been possible using the methods described herein to obtain a 10-million fold expansion of progenitor cells to reticulocytes/mature erythrocytes in a 1 litre system.

Accordingly, in a first aspect the present invention provides an in vitro or ex vivo method of producing a population of lineage committed haematopoietic progenitor, or mature haematopoietic cells, other than cells of the neutrophil lineage, which method comprises the steps of:
(a) providing a population of cells comprising haematopoietic progenitor cells; and
(b) culturing the population of cells in an animal cell culture medium comprising one or more cytokines that differentiate said progenitor cells into lineage committed haematopoietic progenitor and/or mature haematopoietic cells, under conditions of low oxidative stress, the culture medium being agitated when the cells are at a cell density at which oxygen transfer via the surface of the culture medium is insufficient for growth of the progenitor cells and the progeny thereof under static conditions,
to produce a population of lineage committed haematopoietic progenitor, or mature haematopoietic cells, other than cells of the neutrophil lineage.

In a related aspect, the present invention provides an in vitro or ex vivo method of producing a population of lineage committed haematopoietic progenitor, or mature haematopoietic cells, other than cells of the neutrophil lineage, which method comprises the steps of:
(a) providing a population of cells comprising haematopoietic progenitor cells; and
(b) culturing the population of cells in an animal cell culture medium comprising one or more cytokines that differentiate said progenitor cells into lineage committed haematopoietic progenitor and/or mature haematopoietic cells, under static conditions until the cells are at a cell density at which oxygen transfer via the surface of the culture medium is insufficient for growth of the progenitor cells and the progeny thereof under static conditions, and then agitating the culture medium thereafter,
to produce a population of lineage committed haematopoietic progenitor, or mature haematopoietic cells, other than cells of the neutrophil lineage.

In a second aspect, the present invention provides an in vitro or ex vivo method of producing a population of lineage committed haematopoietic progenitor, or mature haematopoietic cells, other than cells of the neutrophil lineage, which method comprises the steps of:
(a) providing a population of cells comprising haematopoietic progenitor cells;
(b) culturing the population of cells in an animal cell culture medium comprising one or more cytokines that differentiate said progenitor cells into lineage committed haematopoietic progenitor and/or mature haematopoietic cells, wherein the cells are cultured under conditions of low oxidative stress when the total cell density is less than from about 100,000 to 200,000 cells per ml; and
(c) agitating the medium once the total cell density is at least about 100,000 to about 200,000 cells per ml,
to produce a population of lineage committed haematopoietic progenitor, or mature haematopoietic cells, other than cells of the neutrophil lineage.

In a related aspect, the present invention provides an in vitro or ex vivo method of producing a population of lineage committed haematopoietic progenitor, or mature haematopoietic cells, other than cells of the neutrophil lineage, which method comprises the steps of:
(a) providing a population of cells comprising haematopoietic progenitor cells;
(b) culturing the population of cells in an animal cell culture medium comprising one or more cytokines that differentiate said progenitor cells into lineage committed haematopoietic progenitor and/or mature haematopoietic cells, wherein the cells are cultured under static conditions when the total cell density is less than from about 100,000 to about 200,000 cells per ml; and
(c) agitating the medium once the total cell density is at least about 100,000 to about 200,000 cells per ml,
to produce a population of lineage committed haematopoietic progenitor, or mature haematopoietic cells, other than cells of the neutrophil lineage.

In a third aspect, the present invention also provides an in vitro or ex vivo method of producing a population of lineage committed haematopoietic progenitor, or mature haematopoietic cells, other than cells of the neutrophil lineage, which method comprises the steps of:
(a) providing a population of haematopoietic progenitor cells;
(b) culturing the progenitor cells at an initial cell density of less than about 20,000 haematopoietic progenitor cells per ml in an animal cell culture medium comprising one or more cytokines that differentiate said progenitor cells into lineage committed haematopoietic progenitor and/or mature haematopoietic cells, under conditions of low oxidative stress, to produce a population of progeny cells at a density of at least about 100,000 cells per ml of medium; and
(c) culturing the population of progeny cells obtained in step (b) in an animal cell culture medium comprising one or more cytokines that differentiate said progenitor cells into lineage committed haematopoietic progenitor and/or mature haematopoietic cells, the medium being agitated,
to produce a population of lineage committed haematopoietic progenitor, or mature haematopoietic cells, other than cells of the neutrophil lineage.

In a related aspect, the present invention further provides an in vitro or ex vivo of producing a population of lineage committed haematopoietic progenitor, or mature haematopoietic cells, other than cells of the neutrophil lineage, which method comprises the steps of:

(a) providing a population of haematopoietic progenitor cells;
(b) culturing the progenitor cells at an initial cell density of less than about 20,000 haematopoietic progenitor cells per ml in an animal cell culture medium comprising one or more cytokines that differentiate said progenitor cells into lineage committed haematopoietic progenitor and/or mature haematopoietic cells, under static conditions, to produce a population of progeny cells at a density of at least about 100,000 cells per ml of medium; and
(c) culturing the population of progeny cells obtained in step (b) in an animal cell culture medium comprising one or more cytokines that differentiate said progenitor cells into lineage committed haematopoietic progenitor and/or mature haematopoietic cells, the medium being agitated, to produce a population of lineage committed haematopoietic progenitor, or mature haematopoietic cells, other than cells of the neutrophil lineage.

In one embodiment the initial culture medium further comprises cells other than haematopoietic progenitor cells such that the total initial cell density is at least about 100,000 cells per ml of medium.

In a fourth aspect, the present invention also provides an in vitro or ex vivo method of producing a population of lineage committed haematopoietic progenitor, or mature haematopoietic cells, other than cells of the neutrophil lineage, which method comprises the steps of:

(a) providing a population of cells comprising haematopoietic progenitor cells;
(b) culturing the population of cells at a total initial cell density of at least about 100,000 cells per ml in an animal cell culture medium comprising one or more cytokines that differentiate said progenitor cells into lineage committed haematopoietic progenitor and/or mature haematopoietic cells, the medium being agitated, to produce a population of lineage committed haematopoietic progenitor, or mature haematopoietic cells, other than cells of the neutrophil lineage.

In one embodiment the initial cell density of haematopoietic progenitor cells is less than about 20,000 cells per ml.

In an alternative embodiment the initial cell density of haematopoietic progenitor cells is at least about 20,000 cells per ml.

The present invention also provides an isolated population of lineage committed haematopoietic progenitor, or mature haematopoietic cells, other than cells of the neutrophil lineage produced by, obtained by or obtainable by the method of the invention. In a related aspect, the present invention also provides an isolated population of lineage committed haematopoietic progenitor, or mature haematopoietic cells selected from the group consisting of megakaryoblasts, promegakaryocytes, megakaryocytes, thrombocytes, proerythroblasts, basophilic erythroblasts, polychromatic erythroblasts, orthochromatic erythroblasts, polychromatic erythrocytes and erythrocytes, basophilic promyelocytes, basophilic myelocytes, basophilic metamyelocytes, basophilic band cells, mature basophils, eosinophilic promyelocytes, eosinophilic myelocytes, eosinophilic metamyelocytes, eosinophilic band cells, mature eosinophils, monoblasts, promonocytes, monocytes, macrophages, myeloid dendritic cells, mast cells, lymphoblasts, prolymphocytes, natural killer cells (large lymphocytes), small lymphocytes, B lymphocytes, plasma cells, T lymphocytes, and combinations thereof.

In a related aspect, the present invention provides a pharmaceutical composition comprising a population of cells of the invention, together with a pharmaceutically acceptable carrier or diluent, wherein the population of cells comprises at least 1 billion cells, preferably in the case of erythrocytes, at least $1\times10^{12}$ cells (about 1 unit).

The present invention further provides a pharmaceutical composition comprising at least about 5 billion ex vivo expanded lineage committed haematopoietic progenitor, or mature haematopoietic cells, other than cells of the neutrophil lineage, together with a pharmaceutically acceptable carrier or diluent. Preferably in the case of reticulocytes/erythrocytes, the composition comprises at least $1\times10^{12}$ cells (about 1 unit).

In a related aspect the present invention provides a pharmaceutical composition comprising at least about 5 billion ex vivo expanded lineage committed haematopoietic progenitor, or mature haematopoietic cells, selected from the group consisting of megakaryoblasts, promegakaryocytes, megakaryocytes, thrombocytes, proerythroblasts, basophilic erythroblasts, polychromatic erythroblasts, orthochromatic erythroblasts, polychromatic erythrocytes and erythrocytes, basophilic promyelocytes, basophilic myelocytes, basophilic metamyelocytes, basophilic band cells, mature basophils, eosinophilic promyelocytes, eosinophilic myelocytes, eosinophilic metamyelocytes, eosinophilic band cells, mature eosinophils, monoblasts, promonocytes, monocytes, macrophages, myeloid dendritic cells, mast cells, lymphoblasts, prolymphocytes, natural killer cells (large lymphocytes), small lymphocytes, B lymphocytes, plasma cells, T lymphocytes and combinations thereof and combinations thereof, together with a pharmaceutically acceptable carrier or diluents.

The present invention also provides a method of increasing the number of haematopoietic cells in a patient, which method comprises administering to the patient a population of cells of the invention or a pharmaceutical composition of the invention.

In a related aspect, the present invention provides a composition comprising a population of cells of the invention for use in increasing the number of haematopoietic cells in a patient. Also provided is the use of a composition comprising a population of cells of the invention in the manufacture of a medicament for use in increasing the number of haematopoietic, cells in a patient.

The methods of the invention can also be used to expand progenitor cell populations to provide for either mature haematopoietic cells (such as terminally differentiated cells) or expanded populations of lineage committed haematopoietic cells (or both). In the case of expanded populations of lineage committed haematopoietic cells, the cells are harvested earlier in the culture process before they have differentiated to become mature haematopoietic cells.

In one embodiment of the various aspects of the invention described above, common myeloid progenitor cells are excluded as lineage committed haematopoietic progenitor cells.

DETAILED DESCRIPTION OF THE INVENTION

Unless defined otherwise, all technical and scientific terms used herein have the same meaning as commonly understood by one of ordinary skill in the art (e.g. in cell culture, chemistry and molecular biology).

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

Throughout this specification, reference to numerical values, unless stated otherwise, is to be taken as meaning "about" that numerical value. The term "about" is used to indicate that a value includes the inherent variation of error for the device and the method being employed to determine the value, or the variation that exists among the study subjects.

The term "low oxidative stress" means that the level of oxidative stress per cell is sufficiently low to avoid causing significant progenitor cell death as a result of the inability of the progenitor cells to repair cellular damage caused by reactive oxygen species. Cell death can be assessed by standard techniques, such as trypan blue exclusion.

The phrase "cells of the neutrophil lineage" as used herein means (in increasing order of maturity) myeloblasts (although these can give rise to other lineages), neutrophilic promyelocytes, neutrophilic myelocytes, neutrophilic metamyelocytes, neutrophilic band cells, mature neutrophils and any intermediate cell stages.

Blood cells arise from haematopoietic stem cells through a series of intermediate cell types, which can be distinguished by their microscopic morphological appearance, including such characteristics as the size of their nuclei, cell size, nuclear/cytoplasmic ratio, presence/absence of granules, and staining characteristics (See *Atlas of Blood Cells: Function and Pathology*, second edition, Zucker-Franklin et al.)

The term "haematopoietic progenitor cells" will be used to refer to stem cells which can give rise to cells of all haematopoietic lineages, and committed haematopoietic progenitor cells derived from such stem cells which can form colonies. Haematopoietic stem cells are pluripotent cells that are capable both of self-renewal and giving rise to all of the haematopoietic lineages. Human HSCs are generally characterised as $CD34^+$, $Thy-1^+$, $Lin^-$, $c-kit^{lo}$ and $CD38^-$, but not all cells that fall within the functional definition of an HSC have this specific combination of cell surface markers, e.g. some human HSCs are known to be $CD34^{lo}$.

HSCs are thought to give rise to one of two committed progenitor cells: the common myeloid progenitor (CMP) or the common lymphoid progenitor. CMP cells give rise to even more lineage restricted progenitor cells, either the granulocyte/monocyte progenitor (GMP) or the megakaryocyte/erythrocyte progenitor (MEP). All of these committed progenitor cells fall within the meaning of the term "committed haematopoietic progenitor cells". GMPs give rise to monocytes (a precursor to macrophages) and granulocytes, including eosinophils, basophils and neutrophils. MEPs give rise to megakaryocytes and erythrocytes. See Weissman et al., 2001, Annu. Rev. Cell Dev. Biol. 17: 387-403 for a description of HSCs and committed progenitors.

Other terminology used to refer to cell types considered to be various committed haematopoietic progenitor cells includes: CFU-T cells (which give rise to T lymphocytes), CFU-B cells (which give rise to B lymphocytes), CFU-Eosin cells (which give rise to eosinophils), CFU-Bas (which give rise to basophils), CFU-GM cells (which give rise to monocytes which in turn develop into macrophages), CFU-Meg cells (which give rise to megakaryocytes), and both BFU-E and CFU-E cells (which give rise to erythrocytes). Earlier examples of committed haematopoietic progenitor cells include CFU-GEMM cells which can give rise to a range of different myeloid lineages.

Initially, as described above, the multipotent stem cells give rise to committed myeloid "progenitor cells" (termed CMP cells) that generate precursors for all myeloid cell lineages, or to committed lymphoid "progenitor cells" (CLPs) that generate precursors for all lymphoid cell lineages. These progenitor cells then undergo a process of successive lineage restriction as they expand in number and differentiate.

The term "mature cells" as used herein includes terminally differentiated cells and non-cellular fragments and cellular fragments thereof such as platelets.

Common Myeloid Precursor-Derived Cells

Cells of the megakaryocyte-specific lineage are, in order of increasing maturity, megakaryoblasts, promegakaryocytes, megakaryocytes and thrombocytes (platelets), as well as any intermediate cell stages.

Cells of the erythrocyte-specific lineage are, in order of increasing maturity, proerythroblasts, basophilic erythroblasts, polychromatic erythroblasts, orthochromatic erythroblasts, polychromatic erythrocyte (reticulocytes) and erythrocytes, as well as any intermediate cell stages.

Cells of the basophil-specific lineage are, in order of increasing maturity, basophilic promyelocytes, basophilic myelocytes, basophilic metamyelocytes, basophilic band cells, mature basophils and any intermediate cell stages.

Cells of the eosinophil-specific lineage are, in order of increasing maturity, eosinophilic promyelocytes, eosinophilic myelocytes, eosinophilic metamyelocytes, eosinophilic band cells, mature eosinophils and any intermediate cell stages.

Cells of the monocyte-specific lineage are, in order of increasing maturity, monoblasts, promonocytes, monocytes and any intermediate cell stages. Monocytes subsequently develop into macrophages or myeloid dendritic cells which are also include within the definition of this lineage.

Common myeloid progenitor cells also give rise to mast cells.

Of the various cell types listed above, mature cells are considered to be the following: megakaryocytes (and platelets derived therefrom), polychromatic erythrocyte (reticulocytes), erythrocytes, mast cells, basophils, eosinophils, monocytes, macrophages and myeloid dendritic cells. The other listed cell types are considered to be lineage committed progenitor cells.

Common Lymphoid Precursor-Derived Cells

CLPs give rise either to lymphoblasts or lymphoid dendritic cells. Lymphoblasts in turn give rise to prolymphocytes, which give rise to natural killer cells (large lymphocytes) or small lymphocytes, which are the precursors of B- and T lymphocytes. B lymphocytes can subsequently mature into plasma cells. Cells of the lymphoid-specific lineage are therefore these listed cells types and any intermediate cell stages.

Of the various cell types listed above, mature cells are considered to be the following: B lymphocytes and T lymphocytes, plasma cells, natural killer cells and lymphoid dendritic cells. The other listed cell types are considered to be lineage committed progenitor cells.

A particular example of development of the erythrocyte lineage is given by way of illustration.

Erythrocyte Development

The first myeloid progenitor (a common progenitor with erythroid, megakaryocytic, granulocytic and monocytic potential) is designated CFU-GEMM for "colony forming unit—granulocyte, erythroid, macrophage and megakaryocyte", also known as CMP as described above. Under conditions designed for expansion of erythrocytes, the CFU-GEMM progenitor, will give rise to a BFU-E progenitor cell, which is otherwise known as a "burst forming unit—erythroid". The term "colony", generally refers to a cell that is capable of giving rise to more than 50 cells as measured in 14 day in vitro assays for clonal growth. Burst refers to large colonies for which a sudden "appearance" of colouration is observed as the cells within in the colony become haemoglobinised.

The BFU-E is a committed progenitor—it is committed to differentiation into erythrocytes only. It is neither capable of differentiating into other types of cells nor is it capable of dedifferentiating into earlier stage progenitor cells. The BFU-E progenitor cell may then differentiate into a CFU-E or "colony forming unit—erythroid". These colonies are characterised by their pigmentation and are distinct from BFU-E in size and morphology, being 8 to 200 cells in size. A proerythroblast is the first of the series of cells that may be referred to as cells specific to the erythroid lineage, as such cells, once allowed to fully develop (differentiate), can only form erythrocytes.

Cells of the erythrocyte-specific lineage are proerythroblasts, basophilic erythroblasts, polychromatic erythroblast, orthochromatic erythroblast, polychromatic erythrocyte (reticulocyte), and erythrocytes. These can be subdivided into "erythrocyte precursor cells" which are defined herein as proerythroblasts, basophilic erythroblasts, polychromatic erythroblast, orthochromatic erythroblast; and enucleated cells of the erythrocyte lineage (also referred to as "mature erythrocytes") which are defined herein as reticulocytes and erythrocytes.

During this progressive, morphological differentiation from stem cells to mature erythrocytes, changes in the surface antigens of these cells can be observed. For example, haematopoietic stem cells, CFU-GEMM and BFU-E are typically $CD34^+$. Haematopoietic cells that differentiate beyond the CFU-E stage are no longer $CD34^+$. In contrast, CD71 positivity is an indicator of lineage restricted erythrocyte progenitor cells whilst Glycophorin A (GPA) is a red cell specific marker. CD71 expression is subsequently down regulated and GPA upregulated as cells of the erythrocyte lineage undergo terminal differentiation. All functional erythrocytes can be characterized as $CD34^-$, $CD71^-$, and $GPA^+$. It should be appreciated, however, that such transitions in cell surface antigen expression are gradual, rather than abrupt, wherein some cells of a particular precursor cell type may be positive and other cells of the same type may be negative for a particular cell-surface antigen. Furthermore, the determination that a particular cell type is positive or negative for a particular cell-surface antigen will depend, in part, upon the particular method used to make that determination. The characterization of cell differentiation by cell-surface antigen expression may be confirmed by other means of characterizing cell differentiation, such as cell morphology.

In addition to changes in morphology and cell-surface antigen expression, as erythrocyte precursor cells differentiate, they lose their capacity to proliferate (divide). In general, the less mature erythrocyte precursor cells, namely the proerythroblasts, basophilic erythroblasts, and polychromatic erythroblasts, retain their ability to proliferate. More mature erythrocyte lineage cells such as the orthochromatic erythroblast, lose their capacity to proliferate. Ultimately the cell nucleus is lost altogether, and the cells will begin to take on their final morphological form as enucleated, biconcave, discoid cells with a mean cell volume of 80-100 fL.

Once differentiation has progressed to the proerythroblast stage, the proerythroblasts undergo terminal differentiation into basophilic erythroblasts, which, in turn, differentiate into polychromatic erythroblasts over a course of about 2-3 days. Within another 2 days or so, polychromatic erythroblasts differentiate into orthochromatic erythroblasts. These in turn differentiate into polychromatic erythrocytes (reticulocytes), extruding the cell nucleus in the process. Ultimately the polychromatic erythrocyte attains the characteristic appearance of a biconcave, enucleated, discoid cell with a half-life of about 60 days (mature erythrocyte).

Sources of Haematopoietic Stem and Progenitor Cells

Haematopoietic stem cells, as discussed above, are cells that can grow and differentiate in the presence of the appropriate growth factors into cells belonging to any one of the haematopoietic lineages, e.g. erythropoietin and IL-3 for the directed differentiation and expansion of erythrocyte lineage cells. Haematopoietic progenitor cells include both stem cells and committed progenitor cells as described above. Particular examples include haematopoietic stem cells such as $CD34^+$ stem cells, lymphoid progenitor cells (e.g. CLP, CFU-T, CFU-B), myeloid progenitor cells (e.g. CMP, CFU-GEMM/CFU-GM) and BFU-E. Preferred progenitor cells are $CD34^+$.

Suitable sources of haematopoietic progenitor cells include embryonic stem cell-derived progenitor cells, umbilical cord blood, bone marrow and peripheral blood, e.g. mobilized peripheral blood, which may be subject to one or more purification steps to purify progenitor cells from other cellular and non-cellular components. In particular, umbilical cord blood, peripheral blood, e.g. mobilized peripheral blood, or other similar sources, may be subject to an initial purification step to separate mononuclear cells (MNCs) from other components e.g. by Ficoll density gradient centrifugation.

In one embodiment, the source of haematopoietic progenitor cells, including purified populations of mononuclear cells, is not subjected to a selection step to increase the relative numbers of haematopoietic progenitor cells in the cell population, for example a selection step based on cell surface markers, e.g. CD34-based selection. Such a source is herein termed "non-enriched". The method of the invention does not require purification of $CD34^+$ cells from other cells and the omission of this step represents a significant cost saving in the overall process.

In an alternative embodiment, the source of haematopoietic progenitor cells is subject to a selection step to increase the relative numbers of haematopoietic progenitor cells in the cell population, for example a selection step based on cell surface markers, such as CD34-based selection. Such a source is herein termed "enriched". Methods for isolating particular cell types e.g. on the basis of cell surface markers are well known in the art (such as the Dynal CD34 Progenitor Cell Selection System (Dynal A. S., Oslo, Norway) or the Miltenyi system described in the examples). One suitable method is described in the examples. In one embodiment, enrichment is performed by selecting for haematopoietic progenitor cells. In an alternative embodiment enrichment is effected by removing one or more types of non-progenitor cells.

Cell Expansion Methodology

The haematopoietic progenitor cells are typically resuspended in a culture medium suitable for the growth of animal cells, especially haematopoietic cells, such as Stemline II Haematopoietic Stem Cell Expansion Medium (Sigma Aldrich) or Iscove's modified Dulbecco's medium (IMDM), supplemented with appropriate biochemical factors that enhance expansion and lineage specification.

The population of haematopoietic progenitor cells are seeded into a culture vessel at the desired starting density. In one embodiment, the initial density of haematopoietic progenitor cells is less than about 20,000 cells per ml of culture medium, for example less than about 15,000 or 12,500 cells per ml of culture medium.

In a particular embodiment the initial density of haematopoietic progenitor cells is less than about 7,500 or 5,000 cells per ml of culture medium, such as from about 1,000 to 3,000 cells per ml of culture medium. Typically, the initial density of haematopoietic progenitor cells is at least about 1,000 cells per ml of culture medium. Alternatively, the initial density of haematopoietic progenitor cells may be at least about 5,000 cells per ml of culture medium, such as from about 7,500 to 15,000 cells per ml of medium.

In one embodiment, the haematopoietic progenitor cells form at least about 50%, such as at least about 70, 80 or 90%, of the cells seeded initially into the culture medium.

In an alternative embodiment, the initial population of cells may include substantial numbers of cells other than haematopoietic progenitor cells. These cells may already be present in the biological source of the haematopoietic progenitor cells and/or may be added to increase the total initial cell density to greater than the values given above in relation to haematopoietic progenitor cells. The total initial cell density may be greater than about 20,000 cells per ml, such as at least about 50,000 or 100,000 cells per ml, for example at least 200,000 or 500,000 cells per ml. In one embodiment the initial total cell density is from about 200,000 to 400,000 cells per ml. In another embodiment, for example where unselected MNCs are used as a source, the total initial cell density may be in the range of from 500,000 to 5 million cells per ml.

The remainder of the cells other than the haematopoietic progenitor cells may derive from the original source of the haematopoietic progenitor cells e.g. cord blood cells, peripheral blood cells, and/or may be derived from a separate source e.g. peripheral blood cells added to the cell culture to bulk out the total cell content.

The initial volume of culture medium is dependant upon the desired cell lineage, expansion potential of the progenitor source for this lineage, and final number of cells required. For example, to produce one unit of erythrocytes ($2\times10^{12}$ cells) from progenitor cell population with an expansion potential of 1-million fold would require $2\times10^6$ cells. At a preferred starting density of $10^4$ cells/ml, this equates to an initial volume of 200 ml. To produce 10 units of erythrocytes from a progenitor cell population with an expansion potential of 4-million fold would require an initial volume of 500 ml at $10^4$ cells/ml. The initial volume of culture medium is typically less than about 5 L, such as less than about 2 L but may be more where large numbers of haematopoietic progenitor cells are available.

The initial volume of culture medium is typically at least about 10 ml, such as at least about 20, 50 or 100 ml, depending on the numbers of haematopoietic progenitor cells available and the desired starting density of haematopoietic progenitor cells. The initial volume of culture medium is typically less than about 5 L, such as less than about 2 L but may be more where large numbers of haematopoietic progenitor cells are available.

Alternatively expressed, the initial volume of the culture medium may be about 10% or less of the final volume when the mature cells are harvested, for example about 7, 5 or 2% or less of the final volume.

The total number of haematopoietic progenitor cells seeded initially into the culture is preferably greater than about 50,000, more preferably greater than about 100,000 or 200,000 cells.

The culture medium is a medium suitable for the growth of animal cells, as described above, supplemented with the biochemical factors required for cell expansion into cells of the desired lineage and, where necessary, subsequent differentiation into the desired mature cell type. The method of the invention is typically based on the use of two types of growth factors. The first type is early acting cytokines. These cytokines are not haematopoietic pathway specific but act on stem cells and progenitor cells to promote growth and expansion. Examples of known early acting cytokines include the c-kit ligand stem cell factor (SCF) and Flt-3 ligand (FL), as well as interleukins 1 to 12 (in particular IL-1, IL-2, IL-3, IL-6, IL-9, IL-10 and IL-12), thrombopoietin (TPO) and tumour necrosis factor alpha (TNFα). These cytokines are generally commercially available from companies such as Stem Cell Technologies, Amgen, Chemicon or can, for example, be produced recombinantly using standard techniques, or by peptide synthesis. Reference to various cytokines herein includes functionally equivalent molecules such as peptide mimetics e.g. TPO peptide mimetics (Cwirla S E, et al. (1997) Peptide Agonist of the Thrombopoietin Receptor as Potent as the Natural Cytokine. *Science* 276:1696-1699; see also WO95/18858 and U.S. Pat. No. 6,835,809.

The second type of cytokines are capable of directing differentiation of cells into a specific haematopoietic lineage. Such cytokines include but are not limited to EPO, G-CSF, GM-CSF, and thrombopoietin. Again, these cytokines are generally commercially available from companies such as Amgen or can, for example, be produced recombinantly using standard techniques, or by peptide synthesis.

The cytokines are present in the culture medium at an amount effective in promoting expansion/differentiation of progenitor cells into cells of the desired lineage, as appropriate. The cytokines are typically added to the culture medium at a concentration per cytokine of from about 1 to 200 ng/ml, such as from about 5 to 100 ng/ml.

The culture medium therefore comprises one or more cytokines that differentiate said progenitor cells into lineage committed haematopoietic progenitor and/or mature haematopoietic cells, typically cells of a specified lineage.

Typically, the culture medium comprises one or more early acting cytokines and one or more cytokines, such as EPO, which promote differentiation of progenitor cells into cells of a specified lineage.

Examples of cytokines used to expand particular lineages are given below:

Megakaryocytes:
TPO, IL-1β, IL-6, IL-9, IL-11, SCF, FGF2, Flt-3 ligand, SDF1α, PDGF
Natural Killer Cells:
IL-2, IL-3, IL-6, IL-7, IL-15, Flt-3 ligand, SCF, G-CSF, GM-CSF, TPO
Monocytes:
IL-3, SCF, MCSF, Flt-3 ligand, TPO
Eosinophils and Basophils:
SCF, Flt-3 ligand, IL-3, IL-5, GM-CSF
Erythrocytes:
EPO, SCF, IL-3, IGF-2, VEGF
Dendritic Cells:
SCF, TPO, IL1β, IL3, IL4, IL6, GM-CSF, TNFα, M-CSF.
B Cells:
IL2, IL4, IL7, IL10, SCF, Flt-3 ligand, CD40 ligand.

The culture vessel may be any form of container suitable for the culture of animal cells, especially haematopoietic cells. Preferably the container is suitable for suspension culture of cells. Since the volume of cell culture will typically increase substantially during the culture process, preferred culture vessels are capable of being used to culture cells in volumes of culture medium allowing for large increases in culture volume, e.g. an order of magnitude increase from about 100 ml to 1 L, from 1 L to 10 L, 10 L to 100 L, or such as from about 100 L to 1000 L, without the need to transfer cells into different culture vessels. However, as some cell lineages have extremely high expansion capacity (millions-fold for erythrocytes), vessels of differing size may be used, transferring from a smaller size to a larger size to allow for increasing culture volume. In this way a "scale-up train" can be established that requires a minimum number of transfers between vessels.

In one embodiment, the culture vessel is disposable or single-use (non reusable).

In a particularly preferred embodiment, the cells are cultured in a collapsible culture vessel, such as a flexible bag. The requirement for collapsibility/flexibility is such that the vessel can be partially or fully inflated. The vessel is typically made of a flexible plastic such as low density polyethylene. A particularly suitable culture vessel is described in U.S. Pat. No. 6,190,913. The plastic bag culture vessels described in U.S. Pat. No. 6,190,913 are available from Wave Biotech, N.J. (Cellbag®) for use with the Wave Bioreactor®, in sizes ranging from 0.1 to 5 L, to 100 to 500 L.

During the first stage of the process when the progenitor cells and their progeny are often at a density at which the cells are particularly sensitive to the effects of oxidative stress, a number of different techniques can be used to reduce the oxidative stress experienced by the progenitor cells and the progeny thereof on a per cell basis.

In one embodiment, the cells are cultured under static conditions, i.e. without agitation, shaking and the like.

In another embodiment, the net effect of oxidative stress per progenitor cell is reduced by increasing the total number of cells in the culture medium using other cells. In this embodiment the initial total cell density is preferably at least about 50,000 or 100,000 cells per ml, more preferably at least about 200,000 or 500,000 cells per ml. In one embodiment the initial total cell density is from about 200,000 to 400,000 cells per ml. In another embodiment, for example where unselected MNCs are used as a source, the total initial cell density may be in the range from 500,000 to 5 million cells per ml.

The remainder of the cells other than the haematopoietic progenitor cells may derive from the original source of the haematopoietic progenitor cells e.g. cord blood cells, peripheral blood cells, and/or may be derived from a separate source e.g. peripheral blood cells added to the cell culture to bulk out the total cell content. These additional cells may also include lineage restricted precursors and mature blood cells.

In a further embodiment, the levels of oxidative stress are reduced by the addition of agents that neutralise reactive oxygen species, i.e. antioxidants and radical scavengers. Examples of such agents that are suitable for animal cell culture include glutathione, 2-mercaptoethanol and other thiol compounds, pyruvate, ascorbate, catalase, serum albumin, and Pluronic F68™.

In another embodiment, the level of oxidative stress is reduced by controlling the oxygen tension in the culture. The normal oxygen tension—in absence of cell metabolism—is around 20% dissolved oxygen (DO) for air with 5% $CO_2$. Preferably the DO content is less than about 10%, such as less than about 5%. In a particular embodiment where the initial progenitor cell density is less than about 5,000 cells per ml and the total initial cell density is less than about 100,000 cells per ml, the DO content is preferably less than about 10%.

In embodiments where the cells are seeded at a relatively low total cell density and oxidative stress is reduced by methods other than by increasing the initial cell density with non-progenitor cells (e.g. by using static cultures), in a first stage the cells are cultured until the desired cell density of haematopoietic progenitor cells and progeny thereof (i.e. cells derived from the progenitor cells by proliferation/differentiation) is reached. In one embodiment, this is considered to be the density at which oxygen transfer via the surface of the culture medium is insufficient for growth of the progenitor cells and/or the progeny thereof under static conditions, i.e. DO is a limiting factor for cell growth.

In another embodiment the cells are cultured until the cell density, typically the density of haematopoietic progenitor cells and progeny thereof, is at least about 50,000 or 100,000 cells per ml, such as from about 100,000 to 400,000 cells per ml or from about 100,000 to 200,000 cells per ml. In another embodiment, the cells are cultured until the cell density is at least about 200,000 cells per ml, such as from about 200,000 to 400,000 cells per ml.

During this initial step, there may be no addition of fresh medium or alternatively, fresh medium may be added. However, where there is no addition of fresh medium, additional nutrients, particularly growth factors, may optionally be added. This initial expansion step typically takes at least about 4 or 5 days, such as from about 4 to 9 days or from about 7 to 9 days.

Once the population of progeny cells has reached the desired cell density, the cells can then be subject to the second step of the culture process. In this second step the progenitor cells have expanded sufficiently and reached a sufficient cell density that they can be cultured under the more vigorous conditions used in large scale cell culture methods. In embodiments where the initial total cell density is already sufficiently high, the first step is effectively omitted and agitation can be performed from the beginning of the culture process.

Agitation of the cells is used in this second step since under static conditions there would be insufficient transfer of oxygen into the culture medium to properly sustain the cells. Similarly, the mixing of nutrients within the culture medium is beneficial to the cells. Accordingly, agitation of the culture medium should commence no later than when the total cell density is such that static culture conditions would provide inadequate cell feeding and growth. This can be determined by a person skilled in the art by, for example, growing the cells under static conditions and observing the point at which the rate of cell growth starts to diminish.

The cells are subject to agitation, such as by stirring, e.g. in a stirred tank-type bioreactor, rolling, e.g. roller bottle cultures, or wave motion, e.g. in a collapsible culture vessel, such as the Cellbag described above, which is subject to rocking. Again, in one embodiment, the culture vessel is disposable or single-use (non reusable).

In more detail, the Cellbag is typically filled with liquid culture medium so that the culture medium comprises between about 10 to 50% of the volume of the bag. As a guide, the volume of liquid media will initially be smaller when dilution feeding is used (to allow room for an increase in culture volume) but can be greater where fresh culture feeding is achieved by perfusion methods or the like. The remainder of the bag is then generally filled with an oxygen-containing gas such that the bag becomes rigid. The bag is generally inflated to allow sufficient headspace between the surface of the culture medium and the top of the bag so that waves can form on the surface of the culture medium when the bag is gently rocked.

The bag is secured to a platform which is rocked in a single degree of freedom to thereby induce a wave motion to the liquid medium in the bag. The necessary oxygen transfer and mixing required for cell growth and productivity is accomplished by the wave motion. The rocking is typically carried out through an angle of from about 1 to 15 degrees from a horizontal position of the platform. The rate of rocking is typically from about 1 to 20 rocks per minute.

There are two main approaches to cell feeding. In one embodiment, the cells can be fed by the addition of fresh media, such that the volume of the culture medium increases during the second stage of the culture process. This is termed dilution feeding. Preferably, feeding is carried out at sufficient intervals to ensure that the total cell density is maintained at less than about 5 million cells per ml, e.g. less than about 4 or 2 million cells per ml of culture medium.

In an alternative embodiment, the volume of the culture medium is kept substantially constant and the cells fed by removal of old medium and replacement with fresh medium, but without removing substantial numbers of viable cells. One suitable method is termed perfusion (e.g. Koller et al., 1993, Blood 82: 378-384), which may be continuous or discontinuous.

In a further embodiment, the two techniques described above can be combined e.g. perfusion is used but the volume of the culture medium is increased over time by adding in more fresh medium than is removed to ensure that the cell density does not increase above a desired level.

It is generally preferred, whichever feeding method is used, to maintain the total number of cells at a minimum density of at least about 400,000 cells or 500,000 cells per ml during the second culture step.

In both stages of culture, the temperature of the culture medium is generally maintained at from about 35 to 39° C., preferably from about 36 to 38° C., such as about 37° C. The optimum $CO_2$ levels are generally from about 3 to 10% $CO_2$, such as from about 4 to 6% $CO_2$, preferably about 5% $CO_2$.

In this second stage, the one or more early cytokines may be different to the first stage.

The cells are cultured for a sufficient time to allow for optimum expansion and production of cells restricted to the desired lineage. The duration of the second phase is dependent on the target mature cell type. In the case of erythrocytes for example, expansion may be maintained for more than 30 days, whereas 5-20 days may be more appropriate for megakaryocytes. The progress of expansion/differentiation can be monitored using standard techniques e.g. aliquots of cells can be taken at intervals and examined under the microscope, following Leishman's staining, to identify mature cells, which have a characteristic morphology. Cells may also be analysed to determine the presence of mature lineage-specific cell surface markers using standard techniques such as fluorescence activated cell sorting (FACS).

Cells may also be tested to determine functional activity. These tests are dependent upon the target cell type. Erythrocytes for example, may be tested for haemoglobin content and type, mean cell volume (MCV), mean cell haemoglobin (MCH), oxygen binding kinetics, and deformability (Hoffman R, et al. (2005) Hematology Basic Principles and Practice, $4^{th}$ Edition. Churchill Livingstone).

Megakaryocytes, or more precisely platelets which are derived from these, may be tested for mean platelet volume (MPV) expression of activation markers (CD62P, CD63), platelet aggregation, and release of platelet granule components (Quinn, M. & Fitzgerald, D. (2005) Platelet function: assessment, diagnosis, and treatment. Humana Press).

Measurements of dendritic cell potency include cytokine secretion, T-cell activation, migration, antigen uptake, and co-stimulatory activity (Robinson, S. P. & Stagg, A. J. (2001) Dendritic Cell Protocols. Humana Press).

Typical functional measures for monocytes and macrophages include cytokine secretion in response to stimulus, phagocytic activity, migration, microbial killing activity, and response to LPS stimulation (Paulnock, D. M. (2000) Macrophages: A Practical Approach. Oxford University Press).

Natural killer cell functionality can be measured by cytokine secretion, migration and cytotoxic activity (Campbell, K. S. & Colonna M. M. D. (1999) Natural killer cell protocols. Humana Press)

T cell functionality can be measured by cytokine secretion, migration, B cell interaction, and cytotoxic activity (Kearse, K P. (2000) T Cell Protocols, Humana Press)

B cell function can be assessed by antibody production, antigen processing, T cell interaction, and migration Gu, H. & Rajewsky, K. (2004) B cell protocols. Humana Press Due to the complex roles that haematopoietic cells play in vivo, an exhaustive list of functional measures is not possible. However, suitable functional tests, or targets for assessing functionality, are readily available in the scientific and medical literature and can be selected by a person skilled in the art.

In some cases, additional cultivation phases may be employed. These additional phases may take place under either static or agitated conditions. In the case of erythrocytes for example, the expansion medium differs from that required for final maturation and functional differentiation. During expansion, SCF and hydrocortisone are included in the medium. These however inhibit maturation and are eliminated from the culture medium to promote terminal differentiation of the expanded cells. Strategies might also be employed where multipotent progenitor cells are first expanded in the absence of strong differentiation cues, followed by medium containing cytokines that promote differentiation to the desired lineage. For example, a combination of TPO, SCF, and Flt-3 ligand might be used to expand the multipotent progenitor pool, followed by addition of GCSF to promote granulocytic differentiation.

In progressing from phase to phase, the medium may be removed (e.g., filtration, dilution, centrifugation) and replaced with the medium appropriate to the following phase, specific medium components may be removed (e.g. through the use of neutralising antibodies, selective adsorption, or degradation), or specific components may be added (direct addition or timed release of a component).

Once the desired extent of expansion and differentiation is achieved, cells can be harvested. Harvested cells are typically washed and resuspended in a medium suitable for therapeutic administration such as platelet storage solutions (e.g., Plasmalyte A or T-Sol—both available from Baxter Healthcare, Deerfield, Ill.).

The results shown herein demonstrate a 5000-fold expansion of haematopoietic progenitor cells to mature neutrophils and a 10 million-fold expansion of haematopoietic progenitor cells to reticulocytes/erythrocytes. Accordingly, it is preferred that the method of the invention results in at least about a 1000-fold expansion, more preferably about a 2000- or 4000-fold expansion of the population of progenitor cells to mature cells of the haematopoietic lineage. The extent of the required expansion will vary depending on the cell type. For example, in the case of erythrocytes it is preferred that the method of the invention results in at least about a million-fold expansion, such as at least 2 or 5 million-fold.

In the case of mature cells, preferably the total number of resulting cells (or non-cellular derivatives or fragments such as platelets) of the haematopoietic lineage obtained is at least 500 million, such as at least 1 billion, more preferably at least 2, 5, 10, 15 or 20 billion (in the case of erythrocytes, preferably at least 200 or 500 billion, such as at least $10^{12}$ cells, equivalent to 0.2, 0.5 and 1 unit respectively). The desired number of cells produced by the method of the invention, both in relation to mature cells and lineage committed progenitor cells can also be expressed in terms of units, a commonly used terminology with respect to blood products. The method of the invention preferably results in the production of least 1 unit of the desired cell type, such at least 2, 5 or 10 units.

Preferably the final volume of the culture medium when the cells are harvested is at least about 10 L, such as at least about 20, 50 or 100 L The methods described above may also be used to obtain an expanded population of haematopoietic progenitor cells, particularly lineage committed progenitor cells. In this embodiment, the cells are harvested at an earlier stage before the majority of progenitor cells have differentiated to produce mature blood cells. The total number of resulting cells will typically be lower when committed progenitor cells are being produced from stem cells than when mature cells are being produced (and therefore the preferred number of total lineage committed progenitor cells may be in the order of at least 1, 2 or 5 million, such as at least 10 or 100 million). The resulting progenitor cells can be subjected to further expansion using, for example, the techniques described herein. The lineage committed progenitor cells may be capable of giving rise to a number of different lineages or may be restricted a single lineage.

The various embodiments, definitions, conditions and aspects described above in relation to the production of mature haematopoietic cells apply mutatis mutandis to the production of expanded populations of haematopoietic progenitor cells (e.g. lineage committed progenitor cells), taking into account in particular that, as mentioned above, cells will be harvested at an earlier stage and that some of the cytokines needed to produce mature cells may not be required.

The present invention also provides a population of expanded populations of haematopoietic progenitor cells, produced by, obtained by, or obtainable by the method of the invention. Such cells include common myeloid precursor cells and common lymphoid progenitor cells. In one embodiment, common myeloid precursor cells and myeloblasts are specifically excluded.

Therapeutic Compositions and Uses Thereof

The method of the invention can be used to provide clinical quantities of mature haematopoietic cells and/or lineage committed haematopoietic progenitor cells for use in treating disorders characterised by loss of functional haematopoetic cells, such as excessive blood loss through trauma or blood diseases such as leukaemia. Accordingly the present invention provides a pharmaceutical composition comprising an isolated population of cells comprising at least about 1 billion mature haematopoietic cells (not including mature neutrophils) more preferably at least about 2, 5, 10, 15 or 20 billion mature haematopoietic cells, together with a pharmaceutically acceptable carrier or diluent. Typically, the cells have been produced by the method of the invention.

The number of cells in the composition can also be expressed in terms of units, a commonly used terminology with respect to blood products. A composition of the invention preferably comprises at least 1 unit of the desired cell type.

In one embodiment, preferably at least about 40%, preferably at least about 50, 60, 70, 80 or 90%, such as at least about 95%, of the cells in the composition are lineage committed haematopoietic progenitor cells, not including cells of the neutrophil lineage.

In another embodiment, preferably at least about 40%, more preferably at least about 50, 60, 70 or 80% of the cells are mature haematopoietic cells, other than mature neutrophils, such as megakaryocytes (and platelets derived therefrom), polychromatic erythrocyte (reticulocytes), erythrocytes, mast cells, basophils, eosinophils, monocytes, macrophages, myeloid dendritic cells, B lymphocytes and T lymphocytes, plasma cells, natural killer cells and lymphoid dendritic cells. Preferably, a population of mature cells of the haematopoietic lineage according to the present invention has at least about 40% or 50% of the biological activity of a population of peripheral blood haematopoietic cells having the same number of cells, more preferably at least about 70, 75, 80 or 90% of the activity. Biological activity in this context is preferably measured as described above for the various cell types.

The populations of haematopoietic cells of the present invention and compositions comprising the same can be used to treat patients in need of increased levels of haematopoietic cells or that could benefit from increased levels of haematopoietic cells, such as to treat a condition associated with a transient or permanent decrease in the number or functionality of haematopoietic cells (e.g. leukaemia).

The compositions of the invention can be administered to a patient by any suitable mode. The preferred routes of administration will be apparent to those of skill in the art, depending on the type of condition to be prevented or treated. Preferred methods of administration include, but are not limited to, intravenous, intraperitoneal, intracoronary, intraarterial, intraarticular, and intraventricular administration, impregnation of a catheter, and direct injection into a tissue.

Haematopoietic cells can be administered with pharmaceutically acceptable carriers or diluents. Examples include, but are not limited to water, saline, phosphate buffered saline, Ringer's solution, dextrose solution, serum-containing solutions, Hank's solution, other aqueous physiologically balanced solutions, oils, esters and glycols. Aqueous carriers can contain suitable auxiliary substances required to approximate the physiological conditions of the recipient, for example, by enhancing chemical stability and isotonicity.

According to the present invention, an effective administration protocol comprises suitable dose parameters and modes of administration that result in delivery of a useful number of functional haematopoietic cells to a patient to provide a transient or long term benefit to the patient. Effective dose parameters can be determined using methods standard in the art for a particular condition or disease. Such methods include, for example, determination of survival rates, side effects (i.e. toxicity) and progression or regression of disease.

A suitable single dose of haematopoietic cells according to the present invention is a dose that is capable of providing a beneficial number of haematopoietic cells to a patient, when administered one or more times over a suitable time period. For example, a preferred single dose of haematopoietic cells according to the present invention is from about $1 \times 10^8$ to about $5 \times 10^{10}$, or $2 \times 10^{12}$ or even $3 \times 10^{12}$ haematopoietic cells per individual per administration, such as from about $1 \times 10^9$ to about $5 \times 10^{10}$. It will be apparent to one of skill in the art that the number of doses administered to a patient is dependent upon the extent of the condition or disease and the response of an individual patient to the treatment. Doses can also be expressed in terms of units, a commonly used terminology with respect to blood products. A single dose will typically be at least 1 unit.

Treatment may include reducing the symptoms of the disease; reducing the occurrence of the disease, and/or reducing the severity of the disease. As such, treatment includes both preventing disease occurrence (prophylactic treatment) and treating an animal that has a disease or that is experiencing initial symptoms of a disease (therapeutic treatment). The term, "disease" refers to any deviation from the normal health of a mammal and includes a state when disease symptoms are present, as well as conditions in which a deviation (e.g., infection, gene mutation, genetic defect, etc.) has occurred, but symptoms are not yet manifest.

In the method of the present invention, population of cells according to the present invention and composition comprising the same can be administered to any animal or human, e.g. mammals such as primates, rodents, livestock and domestic pets.

The present invention will now be described further with reference to the following examples which are illustrative only and non-limiting.

REFERENCE EXAMPLES

The following examples in relation to neutrophils are included to illustrate methodologies subsequently applied to other blood cell types in the actual examples.

Materials and Methods

Cord Blood Collection

Human Umbilical Cord Blood (UCB) samples from full term deliveries were obtained with informed consent of the mothers from the Royal Brisbane and Women's Hospital (Brisbane, Australia). Approximately 30 to 50 ml cord blood was routinely recovered and collected in 50 ml tubes containing 250 IU sodium heparin (DBL). Cord Blood Samples were stored at ambient temperature and processed within 24 hours of collection.

CD34$^+$ Cell Selection

Mononuclear cells (MNC) were separated by density gradient centrifugation over Ficoll-Paque Plus (Amersham) and enriched in CD34$^+$ cells by two rounds of positive selection using the Midi and Mini-MACS columns and Direct CD34$^+$ Progenitor Cell Isolation Kit (Miltenyi Biotech) following the manufacturer's recommendations.

Briefly, cord blood was diluted (1:4) in calcium and magnesium free phosphate-buffered-saline (PBS) containing 2 mM EDTA, layered on a Ficoll-Paque Plus density gradient and centrifuged at 450 g for 30 minutes at ambient temperature to separate the mononuclear cells. The buffy coat was collected, washed and contaminating red blood cells (RBC) removed by ammonium chloride lysis.

Following lysis, cells were washed and resuspended in MACS buffer (PBS+2 mM EDTA+0.5% bovine serum albumin (BSA). The cells were then incubated firstly with the FcR blocking reagent and secondly with the MACS paramagnetic MicroBeads coated with CD34 antibodies from the isolation kit. After the incubation step the cells were washed and passed through a pre-separation filter before being applied to a pre-equilibrated positive selection column (LS+) held in a magnetic field. The column was washed three times with MACS buffer during which time the non-binding unlabelled cells passed through the column while the CD34$^+$ cells were retained within the column. CD34+ cells were recovered by releasing the magnetic field and flushing cells from the column. The eluted cells were washed in MACS buffer and the magnetic separation step was then repeated with cells applied to a second pre-filled positive selection column (MS+). CD34$^+$ cells were used immediately after separation. The typical purity of the CD34$^+$ cells was >90%. Following selection, the CD34$^+$ cells were resuspended in 1 ml Stemline II Haematopoietic Stem Cell Expansion Medium (Sigma Aldrich).

Cytokines

Stem cell factor (rhSCF) and granulocyte colony stimulating factor (rhG-CSF) were obtained from Amgen. Recombinant human thrombopoietin (rhTPO) was obtained from Chemicon. TPO peptide mimetic was obtained from Auspep.

Reference Example 1

Ex Vivo Expansion of Neutrophil Progenitor Cells—Effect of Cell Density and Agitation Following purification and selection as described above, CD34$^+$ cells from UCB were resuspended in 1 ml Stemline II Haematopoietic Stem Cell Expansion Medium (Sigma Aldrich) and seeded into T-flasks at a density of either 2,000 cells per ml or 10,000 cells per ml.

Cells were seeded in Neutrophil Complete Media (Stemline II supplemented with stem cell factor (rhSCF) 100 ng/ml, granulocyte colony stimulating factor (rhGCSF) 100 ng/ml and 100 ng/ml TPO peptide mimetic.

Cells were incubated for 12 days in an incubator at 37° C., 5% $CO_2$, either with rocking (15 rocks/min, 8° angle) or without rocking (static).

The results obtained showed that rocking reduced expansion by 20- to 50-fold. Rocking therefore had a significant, adverse impact on the levels of expansion of haematopoietics from progenitor cells, although the effect was less severe with cells seeded at the higher density.

The experiment was repeated but with the cells being cultured under static conditions for 9 days followed by rocking from day 9 onwards. The results showed that there was no difference in the levels of expansion between cultures that were static for the entire course of the experiment and those that were rocked after day 9. From measurements of cell density, we conclude that the deleterious effects of agitation can be avoided if cells are allowed to reach a minimum cell density e.g. at least about 100,000 to 200,000 cells per ml, prior to agitation.

Reference Example 2

Effect of Dissolved Oxygen (DO) Levels on Vivo Expansion of Neutrophil Progenitor Cells Following purification and selection as described above, CD34$^+$ cells from umbilical cord blood were resuspended in 1 ml Stemline II Haematopoietic Stem Cell Expansion Medium (Sigma Aldrich) and seeded in Neutrophil Complete Media into T-flasks at a density of either 2,000 cells per ml or 10,000 cells per ml.

Cells were incubated under conditions of either low dissolved oxygen (5%) or high dissolved oxygen (20%). At the lower cell density of 2,000 cells per ml, the levels of expansion seen were significantly lower with high DO versus low DO. However, no significant difference was seen when cells were seeded at the higher cell density. We suggest that this is due to the effects of oxidative stress on the cells, these effects being proportionately greater for a given level of DO when lower numbers of cells are used initially.

There are several approaches that could be used to reduce the levels of oxidative stress experienced by the cells. Firstly, the initial cell density could be increased. Since it is preferred not to seed the progenitor cells themselves at high density, one way to achieve higher cell density without the need for using larger numbers of progenitor cells is to bulk the progenitor cells out with non-progenitor cells, such as peripheral blood cells. Another approach is to culture the cells under static conditions until the density of progeny cells reaches the desired minimum cell density prior to commencing agitation—as demonstrated in Reference Example 4. A further possibility is to adjust the media formulation to include ingredients that scavenge oxygen radicals and/or to regulate the oxygen tension.

Reference Example 3

Comparison of rhTPO with TPO Peptide Mimetic

Following purification and selection as described above, CD34+ cells from umbilical cord blood were resuspended in 1 ml Stemline II Haematopoietic Stem Cell Expansion Medium (Sigma Aldrich) and seeded into T-flasks at a density of 2,000 cells per ml.

Cells were seeded in Neutrophil Complete Media. The source of TPO was either recombinant human thrombopoietin at 100 ng/ml, or TPO peptide mimetic at 4, 20 or 100 ng/ml.

Cells were incubated for 12 days in an incubator at 37° C., 5% $CO_2$ under static conditions Similar results were obtained using concentrations of 20 ng/ml and 100 ng/ml of TPO peptide mimetic or rhTPO, demonstrating that TPO peptide is as potent as rhTPO. Since TPO peptide mimetic is significantly less expensive than rhTPOs, the use of the TPO peptide is advantageous in terms of cost.

Reference Example 4A

Ex Vivo Expansion of Neutrophil Progenitor Cells in CellBags

Materials and Methods

Following purification and selection as described above, CD34+ cells from umbilical cord blood were resuspended in 1 ml Stemline II Haematopoietic Stem Cell Expansion Medium (Sigma Aldrich). Cells were counted using a haemocytometer and cultured ex vivo for up to 17 days in a 2 L FEP CellBag as part of the Wave Bioreactor System (Wave Biotech) as described below.

Cells were seeded at 200,000 cells/20 ml total volume in Neutrophil Complete Media (TPO source was TPO peptide mimetic at 100 ng/ml).

Cells were applied to the cellbag at 2× the seeding density in 10 ml haematopoietic complete media via a luer lock sample port on the bag and this was followed by 10 mL fresh media to wash the cells from the tubing taking the density and volume to the appropriate level. The cellbag was not inflated at this point and was placed in the incubator at 37° C., 5% $CO_2$ in a fully humidified atmosphere and left static and untouched until Day 5 of culture. In parallel 10 ml of the same 2× density cell suspension was added to the flask along with 10 ml fresh media and was incubated under the same conditions, not touched until Day 5.

At Day 5, the medium in the cellbag was diluted by adding an equal volume of fresh medium (half-dilution), i.e. 20 ml.

At Day 7, the medium in the cellbag was diluted by adding an equal volume of fresh medium (half-dilution), i.e. 40 ml.

At Day 9 and every other day thereafter (11, 13, 15), the cellbag was diluted back to about 500,000 cells/ml with fresh medium. Moreover, the cellbag was inflated by continuous aeration (0.1 L/min) and the cultures gently rocked (5 rocks/min, 7° angle) for the remainder of the culture period.

Samples for analysis were withdrawn every other day starting from day 5 from both vessels after a thorough mixing of the cultures. Cells were counted using a haemocytometer to determine cell density and viability. Cell viability was assessed microscopically using trypan blue to distinguish viable from non-viable cells.

Cytospin preparations of cultured cells were prepared on days 13, 15 and/or days that coincided with functional testing using a cytocentrifuge attachment for a Sigma centrifuge with $1\times10^5$ cells per slide. The slides were fixed with Leishman's stock for 2 mins and stained for 8 mins in a 1:6 dilution of Leishman's stock in pH 6.8 phosphate buffer. The slides were then evaluated for the presence of myeloblasts, promyelocytes, myelocytes, bands and segmented neutrophils. The presence of mitotic, apoptotic and other cell populations was also noted.

Results

At day 16, the final culture volume was about 1000 ml with a cell density of about 1,000,000 cells per ml following the final dilution, giving a total of 1000 million cells in a volume of 1000 ml. Since the initial culture containing 200,000 cells in 20 ml, the fold increase in expansion as determined by cells final/cells initial was about 5000-fold. This is a significantly greater degree of expansion than has been obtained previously using other techniques.

The population of expanded cells were also tested for neutrophil function. The results obtained indicated that the neutrophils were not activated (i.e. were safe to infuse) but had the ability to become activated in the presence of appropriate stimuli. They had superoxide function (ability to kill bacteria) at the lower limit of normal when compared with normal peripheral blood neutrophils.

The cells also appeared to express normal levels of HLA Class I antigens and haematopoietic specific antigens, indicating that they are fully mature cells. An automated 5 part machine differential count on the day 16 and day 18 cultures demonstrated that 80% of cells were mature or post-mitotic neutrophils. This was confirmed by manual differential counts of a total of 200 cells on Giemsa stained smears.

Accordingly, not only was significant cell expansion obtained, but the resulting cells were both at a mature, post-mitotic stage and functional.

For comparison, a control experiment was run using a low density polypropylene Cellbag or Teflon cellbag where the cells were agitated and headspace aeration used for the entire duration of the experiment. This reflects the typical conditions used in a bioreactor scale-up. The results obtained in the control experiment showed poor levels of expansion, in the region of 100-fold. It can therefore be seen that the method of the invention results in significantly better expansion of haematopoietic cells, when scaled up to volumes of over a litre than existing bioreactor-based cell culture and expansion methodologies.

Reference Example 4B

Ex Vivo Expansion of Neutrophil Progenitor Cells in Cell Bags

Materials and Methods

Following purification and selection as described above, CD34+ cells from umbilical cord blood were resuspended in 1 ml Stemline II Haematopoietic Stem Cell Expansion Medium (Sigma Aldrich). Cells were counted using a haemocytometer and cultured ex vivo for up to 17 days in a two step process. In the first step, cells were cultivated under static conditions in a gas permeable FEP cell culture bag. In the second phase, cells were transferred to an LDPE cell bag as part of the Wave Bioreactor System (Wave Biotech).

Cells were seeded into the gas permeable FEP cell culture bag at 200,000 cells/20 ml total volume in Neutrophil Complete Media (TPO source was TPO peptide mimetic at 100 ng/ml), via a luer lock port on the bag. The FEP bag was placed in the incubator at 37° C., 5% $CO_2$ in a fully humidified atmosphere and left static and untouched until Day 5 of culture. In parallel 10 ml of the same cell suspension (100,000 cells/10 mL total volume) were added to a 25 $cm^2$ tissue culture flask and incubated under the same conditions, untouched until Day 5.

At Day 5, the medium in the FEP bag was diluted by adding an equal volume of fresh medium (half-dilution), i.e. 20 ml. Flask cultures were similarly diluted 1 in 2.

At Day 7, the medium in the FEP was diluted by adding an equal volume of fresh medium (half-dilution), i.e. 40 ml. Flask cultures were similarly diluted 1 in 2.

At Day 9 the content of the FEP bag were transferred to the LDPE bag with a volume of fresh medium sufficient to dilute the cell concentration to 500,000 cells/ml. Every other day thereafter (11, 13, 15), the LDPE bag was diluted back to about 500,000 cells/ml with fresh medium. Moreover, the cellbag was inflated by continuous aeration (0.1-0.2 L/min) and the cultures gently rocked (6 rocks/min, 7° angle) for the remainder of the culture period. Flask cultures were maintained under static conditions in flasks following the same regime of fresh media addition as for bag cultures.

Samples for analysis were withdrawn every other day starting from day 5 from both vessels after a thorough mixing of the cultures. Cells were counted using a haemocytometer to determine cell density and viability. Cell viability was assessed microscopically using trypan blue to distinguish viable from non-viable cells.

Cytospin preparations of cultured cells were prepared on days 13, 15 and/or days that coincided with functional testing using a cytocentrifuge attachment for a Sigma centrifuge with $1\times10^5$ cells per slide. The slides were fixed with Leishman's stock for 2 mins and stained for 8 mins in a 1:6 dilution of Leishman's stock in pH 6.8 phosphate buffer. The slides were then evaluated for the presence of myeloblasts, promyelocytes, myelocytes, bands and segmented neutrophils. The presence of mitotic, apoptotic and other cell populations was also noted.

Results

At day 15, the final culture volume was about 1000 ml with a cell density of about 1,000,000 cells per ml following the final dilution, giving a total of 1000 million cells in a volume of 1000 ml. Since the initial culture containing 200,000 cells in 20 ml, the fold increase in expansion as determined by cells final/cells initial was about 5000-fold. This is a significantly greater degree of expansion than has been obtained previously using other techniques.

The population of expanded cells comprised about 40% band and segmented neutrophils, as determined by manual differential counts of a total of 200 cells on Leishman's stained cytospin preparations.

Reference Example 5

Expansion of Non-Enriched Sources of Progenitor Cells

The methodology described in Reference Example 4 was repeated with the exception that the mononuclear cells obtained after purification of cord blood on a Ficoll-Paque Plus density gradient were used directly with no CD34+ enrichment step. Cells were seeded at an initial density of 2000 CD34+ cells per ml in 15 to 20 ml of culture medium. The total cell density depended on the particular cord used (range 150,000 to 500,000 cells per ml), the remainder of the cells being other types of blood cells).

The results obtained with non-enriched cell populations were significantly better than those obtained with cell populations enriched for CD34+ cells (10,000-fold, non-selected, at day 15 versus 6,000-fold at day 15, selected).

EXAMPLES

Materials and Methods

Cord Blood Collection

Human Umbilical Cord Blood (UCB) samples from full term deliveries were obtained with informed consent of the mothers from the Royal Brisbane and Women's Hospital (Brisbane, Australia). Approximately 30 to 50 ml cord blood was routinely recovered and collected in 50 ml tubes containing 250 IU sodium heparin (DBL). Cord Blood Samples were stored at ambient temperature and processed within 24 hours of collection.

$CD34^+$ Cell Selection

Mononuclear cells (MNC) were separated by density gradient centrifugation over Ficoll-Paque Plus (Amersham) and enriched in $CD34^+$ cells by two rounds of positive selection using the Midi and Mini-MACS columns and Direct $CD34^+$ Progenitor Cell Isolation Kit (Miltenyi Biotech) following the manufacturer's recommendations.

Briefly, cord blood was diluted (1:4) in calcium and magnesium free phosphate-buffered-saline (PBS) containing 2 mM EDTA, layered on a Ficoll-Paque Plus density gradient and centrifuged at 450 g for 30 minutes at ambient temperature to separate the mononuclear cells. The buffy coat was collected, washed and contaminating red blood cells (RBC) removed by ammonium chloride lysis.

Following lysis, cells were washed and resuspended in MACS buffer (PBS+2 mM EDTA+0.5% bovine serum albumin (BSA). The cells were then incubated firstly with the FcR blocking reagent and secondly with the MACS paramagnetic MicroBeads coated with CD34 antibodies from the isolation kit. After the incubation step the cells were washed and passed through a pre-separation filter before being applied to a pre-equilibrated positive selection column (LS+) held in a magnetic field. The column was washed three times with MACS buffer during which time the non-binding unlabelled cells passed through the column while the $CD34^+$ cells were retained within the column. $CD34^+$ cells were recovered by releasing the magnetic field and flushing cells from the column. The eluted cells were washed in MACS buffer and the magnetic separation step was then repeated with cells applied to a second pre-filled positive selection column (MS+). $CD34^+$ cells were used immediately after separation. The typical purity of the $CD34^+$ cells was >90%. Following selection, the $CD34^+$ cells were resuspended in 1 ml Stemline II Haematopoietic Stem Cell Expansion Medium (Sigma Aldrich).

Media and Supplements

Stem cell factor (rhSCF) was obtained from Amgen, erythropoietin (rhEPO) from Silag-Janssen, and Interleukin-3 (rhIL3) from Prospec-Tany Technogene. Insulin (rhIN), hydrocortisone (HC), fatty acid free bovine serum albumin (BSA), ferrous nitrate (FN), ferrous sulphate (FS), and holo-transferrin (TF) were obtained from Sigma-Aldrich. Isacove's Modified Dulbecco's Medium (IMDM), Glutamax, and Antibiotic-Antimycotic mix were obtained from Invitrogen.

Example 1

Ex Vivo Expansion of Human Erythroid Cells from Haematopoietic Progenitor Cells Following purification and selection as described above, CD34$^+$ cells from UCB were resuspended in 1 ml IMDM and seeded into T-flasks at a density of 10,000 cells per ml.

Cells were seeded in Erythroid Expansion Media (IMDM supplemented with rhSCF 100 ng/ml, rhEPO 3 IU/ml, rhIL3 5 ng/ml, 1% BSA, 120 µg/ml TF, 10 µg/ml rhIN, $10^{-6}$ M HC, 900 ng/ml FS, 90 ng/ml FN, 2 mM Glutamax, and 1× Antibiotic-Antimycotic mix).

Cells were incubated for 4 days in an incubator at 37° C., 5% $CO_2$, and on the fourth day diluted 1 in 5 with fresh Erythroid Expansion Media.

Following a further 4 days incubation in the above conditions (8 days in total) the culture was diluted with fresh medium such that a final cell density of $1 \times 10^5$ cells/ml was obtained. Two hundred millilitres of this suspension was transferred to 2 L Wave bag and rocked gently at 7 rpm and an angle of 7°, at 37° C. with 5% $CO_2$ in air. At the same time, 3 ml of cell suspension was transferred to a single well of a 6-well plate and similarly maintained under static conditions.

On day 11, 14, and 17, the cell concentration was diluted back to $1 \times 10^5$ cells/ml using fresh Erythroid Expansion Media.

On day 21, cell suspension from the Wave bioreactor was harvested. The cells were pelted by centrifugation, washed using IMDM, and resuspended Erythrocyte Maturation Media (IMDM supplemented with 3 IU/ml rhEPO, 5 ng/ml rhIL3, 1% BSA, 120 mg/ml TF, 10 mg/ml rhIN, 900 ng/ml FS, 90 ng/ml FN, 2 mM Glutamax, and 1× Antibiotic-Antimycotic mix). One litre of this cell suspension was returned to the Wave bag (after thorough rinsing with IMDM), and the culture was rocked at 25 rpm at an angle of 7°.

Cells from static culture were similarly harvested, washed and resuspended and returned to static culture flasks.

Cultures were maintained for a further 6 days to induce terminal differentiation of erythrocytes.

Cells expanded and matured in the wave bioreactor achieved a fold increase in total cell number of approximately 10-million fold, the final cell population comprising 9% orthochromatic erythroblasts and 91% reticulocytes (enucleated erythroid cells). This compares with a composition of 36% polychromatic erythroblasts, 33% orthochromatic erythroblasts, and 30% reticulocytes for cultures expanded and matured under static conditions.

Whilst a slightly larger fold expansion was seen for the static culture, the volume of the culture and the number of cells obtained was much lower than for the wave bioreactor. To achieve the same volume culture (1 L) in the static system would have required a medium-air interfacial area of some 2,500 cm$^2$, or one hundred T25 tissue culture flasks. In the context of generating clinically useful numbers of erythroid cells, a single unit of cells ($2 \times 10^{12}$ cells) in static culture would require some 5000 m$^2$ of interfacial area. This is clearly not feasible.

Consideration of the final culture composition indicates additional advantages of a bioreactor system for expansion and differentiation of RBC. Reticulocytes, the last discernable stage before a mature erythrocyte, comprised 91% of Wave culture versus only 30% for static cultures. The expansion and differentiation of red blood cells is known to be modulated by dissolved oxygen concentrations, low DO promoting expansion and high DO promoting differentiation. Enhanced aeration, and higher DO in the Wave bioreactor culture is likely to promote terminal differentiation of red blood cells.

Cultivation in an agitated bioreactor system permits more compact geometries, and offers the additional possibility of increasing cell densities through the application of advanced culture techniques (e.g. perfusion, on-line control of pH and DO, and continuous feed regimes). The use of the methodology described herein enables for the first time the ability to obtain the required degree of expansion in the more demanding environment of an agitated bioreactor system.

For abundant starting cell sources (e.g., hES cell derived progenitors cells, progenitor cell donations from adults, preexpanded progenitor cells, and multiple donors) where large scale culture is appropriate, method 2 exemplifies a protocol to be considered in translation from static cultivation methods to mixed culture environments. Careful consideration of initial cell densities and growth kinetics are used to find an optimum balance between the expansion enhancing benefits of initial low cell densities, and environmental stresses that can arise due to fluid mixing in large scale culture processes. As medium formulations are modified and growth kinetics change, cell densities and feed profile are adjusted to match these changes.

The various features and embodiments of the present invention, referred to in individual sections above apply, as appropriate, to other sections, mutatis mutandis. Consequently features specified in one section may be combined with features specified in other sections, as appropriate.

All publications mentioned in the above specification are herein incorporated by reference. All of the compositions and/or methods disclosed and claimed in this specification can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

The invention claimed is:

1. An in vitro or ex vivo method of producing a population of lineage committed haematopoietic progenitor or mature haematopoietic cells other than cells of the neutrophil lineage, which method comprises the steps of:
   (a) providing a population of cells comprising haematopoietic progenitor cells; and
   (b) culturing the population of cells in an animal cell culture medium comprising one or more cytokines that differentiate said progenitor cells into lineage committed haematopoietic progenitor and/or mature haematopoietic cells, under static conditions until the cells are at a cell density at which oxygen transfer via the surface of the culture medium is insufficient for growth of the progenitor cells and progeny thereof under static conditions, and then agitating the culture medium thereafter, to produce a population of lineage committed haematopoietic progenitor or mature haematopoietic cells other than cells of the neutrophil lineage.

2. The method of claim 1, wherein the culture medium is agitated once the total cell density is at least about 100,000 to about 200,000 cells per ml.

3. The method of claim 1, wherein the population of cells of step (b) is at an initial cell density of less than about 20,000 haemotopoietic progenitor cells per ml.

4. The method of claim 1, wherein the initial culture medium of step (b) further comprises cells other than haematopoietic progenitor cells such that the total initial cell density is at least about 100,000 cells per ml of medium.

5. The method of claim 4, wherein the cells other than haematopoietic progenitor cells are peripheral blood mononuclear cells.

6. The method of claim 1, wherein the cells are cultured in a collapsible culture vessel and wherein the culture vessel is partly or fully inflated and the agitation of the vessel generates a wave motion in the culture medium.

7. The method of claim 1, wherein the population of haematopoietic progenitor cells has been enriched.

8. A method of increasing the number of haematopoietic cells in a patient, the method comprising:
(a) providing a population of cells comprising haematopoietic progenitor cells;
(b) culturing the population of cells in an animal cell culture medium comprising one or more cytokines that differentiate said progenitor cells into lineage committed haematopoietic progenitor and/or mature haematopoietic cells, under static conditions until the cells are at a cell density at which oxygen transfer via the surface of the culture medium is insufficient for growth of the progenitor cells and progeny thereof under static conditions, and then agitating the culture medium thereafter, to produce a population of lineage committed haematopoietic progenitor or mature haematopoietic cells other than cells of the neutrophil lineage; and
(c) administering to the patient the population of lineage committed haematopoietic progenitor or mature haematopoietic cells other than cells of the neutrophil lineage obtained in step (b) such that the number of haematopoietic cells in the patient is increased.

9. The method of claim 8, wherein the population of cells comprising haematopoietic progenitor cells is obtained from the patient.

10. The method of claim 1, wherein the population of haematopoietic progenitor cells is provided as a non-enriched population of mononuclear cells.

* * * * *